(12) United States Patent
Finley

(10) Patent No.: US 11,529,150 B2
(45) Date of Patent: Dec. 20, 2022

(54) DRILL GUIDE FOR ORTHOPEDIC DEVICE

(71) Applicant: Zimmer, Inc., Warsaw, IN (US)

(72) Inventor: Adam Finley, Warsaw, IN (US)

(73) Assignee: ZIMMER, INC., Warsaw, IN (US)

( * ) Notice: Subject to any disclaimer, the term of this patent is extended or adjusted under 35 U.S.C. 154(b) by 0 days.

(21) Appl. No.: 16/961,832

(22) PCT Filed: Feb. 27, 2019

(86) PCT No.: PCT/US2019/019843
§ 371 (c)(1),
(2) Date: Jul. 13, 2020

(87) PCT Pub. No.: WO2019/168988
PCT Pub. Date: Sep. 6, 2019

(65) Prior Publication Data
US 2021/0077127 A1    Mar. 18, 2021

Related U.S. Application Data

(60) Provisional application No. 62/636,073, filed on Feb. 27, 2018.

(51) Int. Cl.
*A61B 17/17* (2006.01)
*A61B 17/80* (2006.01)

(52) U.S. Cl.
CPC ........ *A61B 17/1728* (2013.01); *A61B 17/809* (2013.01)

(58) Field of Classification Search
None
See application file for complete search history.

(56) References Cited

U.S. PATENT DOCUMENTS 5,601,553 A * 2/1997 Trebing ................. A61B 17/15
411/399
9,113,970 B2 * 8/2015 Lewis ................ A61B 17/1728
(Continued)

FOREIGN PATENT DOCUMENTS

AU    2019227788 A1    7/2020
DE    112019001027 T5    11/2020
(Continued)

OTHER PUBLICATIONS

International Search Report and Written Opinion of the International Searching Authority for International Application No. PCT/US2019/019843 dated May 31, 2019.

(Continued)

*Primary Examiner* — Anu Ramana
(74) *Attorney, Agent, or Firm* — Schwegman Lundberg & Woessner, P.A.

(57) ABSTRACT

A bone plate system for use with fasteners for fixation of a fractured bone, including a bone plate having an elongate shaft for placement against the bone. The bone plate further has at least one threaded hole for receiving at least one fastener, with each hole having a central axis. The plate further has a bone contacting first surface, an opposite second surface, a thickness extending in a dimension between said first and second surfaces; and at least one tubular drill guide cap. The drill guide cap is engageable with a first hole of at least one threaded hole, the cap having a threaded exterior, an internal bore, a proximal end, and a distal end.

7 Claims, 5 Drawing Sheets

(56) References Cited

U.S. PATENT DOCUMENTS

| | | | |
|---|---|---|---|
| 9,730,742 B2* | 8/2017 | Lewis | A61B 17/88 |
| 9,833,270 B2* | 12/2017 | Zlotolow | A61B 17/809 |
| 10,117,689 B2* | 11/2018 | Zlotolow | A61B 17/80 |
| 10,130,403 B2* | 11/2018 | Lewis | A61B 17/8047 |
| 2006/0015123 A1 | 1/2006 | Fencl et al. | |
| 2007/0233111 A1 | 10/2007 | Orbay et al. | |
| 2008/0015591 A1 | 1/2008 | Castaneda et al. | |
| 2009/0118770 A1 | 5/2009 | Sixto, Jr. et al. | |
| 2011/0015682 A1* | 1/2011 | Lewis | A61B 17/88 |
| | | | 606/305 |

FOREIGN PATENT DOCUMENTS

| | | |
|---|---|---|
| GB | 2585283 A | 1/2021 |
| GB | 2585283 B | 2/2022 |
| JP | 2021513909 A | 6/2021 |
| WO | WO-2019168988 A1 | 9/2019 |

OTHER PUBLICATIONS

"International Application Serial No. PCT/US2019/019843, International Preliminary Report on Patentability dated Sep. 3, 2020", 6 pgs.

"United Kingdom Application Serial No. 2012653.8, Examination Report under Section 18(3) dated Aug. 31, 2021", 4 pgs.

"United Kingdom Application Serial No. 2012653.8, Intention to Grant under Section 18(4) dated Nov. 16, 2021", 2 pgs.

"United Kingdom Application Serial No. 2012653.8, Response filed Oct. 1, 2021 to Examination Report under Section 18(3) dated Aug. 31, 2021", 8 pgs.

* cited by examiner

DRILL GUIDE FOR ORTHOPEDIC DEVICE

CROSS REFERENCE

This Application is a U.S. national phase entry under Section 371 of International Application No. PCT/US2019/019843 filed Feb. 27, 2019 and published in English as WO 2019/168988 A1, which claims the benefit of priority under 35 U.S.C. § 119(e) to U.S. Provisional Patent Application Ser. No. 62/636,073 filed Feb. 27, 2018. The contents of each of the prior applications are incorporated by reference herein.

BACKGROUND OF THE INVENTION

Technical Field

This invention relates broadly to surgical devices. More particularly, this invention relates to orthopedic implants, and specifically to bone plates and drill guides.

Background Information

Improper treatment of a fracture to the metaphysis of a long bone can result in deformity and long-term discomfort. Alignment and fixation of a metaphyseal fracture are typically performed by one of several methods: casting, external fixation, pinning, and plating.

Casting is non-invasive, but it may not be able to maintain alignment of the fracture where many bone fragments exist. Therefore, as an alternative, external fixators may be used.

External fixators utilize a method known as ligamentotaxis, which provides distraction forces across the joint and permits the fracture to be aligned based upon the tension placed on the surrounding ligaments. However, while external fixators can maintain the position of the wrist bones, it may nevertheless be difficult in certain fractures to first provide the bones in proper alignment. In addition, external fixators are often not suitable for fractures resulting in multiple bone fragments.

Pinning with K-wires (Kirschner wires) is an invasive procedure whereby pins are positioned into the various fragments. This is a difficult and time-consuming procedure that provides limited fixation if the bone is comminuted or osteoporotic.

Plating utilizes a stabilizing metal plate typically placed against the bone, fixed-angle pegs (which may have threaded or non-threaded shafts) positioned through the plate and entering drilled holes adjacent an articular bone surface, and cortical screws extending from the plate into holes drilled in the bone to provide stabilized fracture fixation.

When fixed-angle pegs are utilized in conjunction with a bone plate, it is necessary to ensure that the pilot holes drilled for the pegs are co-axial with the hole axes. Otherwise, the shaft of the pegs will not properly align with the anatomy, and the head of the pegs will not properly align with the threaded holes of the plate, potentially resulting in cross-threading. As a result, with the plate placed upon the bone, prior to drilling each hole in the bone in alignment with a peg hole, a drill guide is attached to the plate at the peg hole. The guide defines a tubular passage which directs the drill bit in the proper orientation for a peg through the particular peg hole. After drilling each hole, the drill guide is removed, the peg is inserted in the peg hole, and the drill guide is coupled to a subsequent peg hole.

The process of attaching the drill guide during the surgical procedure is laborious. It can be difficult to locate the appropriate angle for threadably coupling the guide to the peg hole during the procedure, given that each peg hole may have a discrete axis angle from the other peg holes. Such difficulty can unnecessarily prolong the surgical procedure. Additionally, in many systems, even systems in which the drill guide is built into the peg, the profile of the system is too tall for use in all situations.

What is needed in the art is plugs that are preassembled and supplied sterile on the plate so that the drill guide is built into the removal tool instead of the plug and wherein the plug is adaptable to a variety of plate thicknesses so that the same plug/peg/insert can be used for all plates in a system instead of having to fit specific inserts to a specific plate thickness.

SUMMARY OF THE INVENTION

A bone plate system for use with fasteners for fixation of a fractured bone, includes a bone plate having an elongate shaft for placement against the bone. The bone plate further has at least one threaded hole for receiving at least one fastener, with each hole having a central axis. The plate further has a bone contacting first surface, an opposite second surface, a thickness extending in a dimension between the first and second surfaces; and at least one tubular drill guide cap. The drill guide cap is engageable with a first hole of at least one threaded hole, the cap having a threaded exterior, an internal bore, a proximal end, and a distal end.

A bone plate system for use with fasteners for fixation of a fractured bone, includes a bone plate having an elongate shaft for placement against a bone The bone plate further has at least one threaded hole for receiving at least one fastener, with each hole having a central axis. The plate further has a bone contacting first surface, an opposite second surface, a thickness extending in a dimension between the first and second surfaces, and at least one tubular drill guide cap. The drill guide cap is engageable with a first hole of at least one threaded hole, the cap having a threaded exterior, an internal bore, a proximal end, and a distal end. A cap removal tool, having a proximal end, a tool longitudinal axis and a distal end, the tool longitudinal axis and the central axis being coaxial, with the distal end shaped to engage the proximal end of the cap, with the cap and the tool being releasably connectable.

A method for fixing a fractured bone includes providing alignment caps prepackaged on a bone plate. An extraction tool, having a tool longitudinal axis and an extraction tool bore in the direction of the tool longitudinal axis, is placed into the drill guide cap, the cap having a central axis, to align the central axis with the extraction tool longitudinal axis. The extraction tool is used to guide a drill, the drill having a drill bit inserted into the extraction tool bore. Preparing the bone using the drill. Removing the drill. Using the extraction tool to remove the alignment drill guide.

These, and other objects, features and advantages of this invention will become apparent from the following detailed description of the various aspects of the invention taken in conjunction with the accompanying drawings.

BRIEF DESCRIPTION OF THE DRAWINGS

The present invention will be understood more fully from the detailed description given hereinafter and from the accompanying drawings of the preferred embodiment of the In the drawings.

Corresponding reference characters indicate corresponding parts throughout the several views. The exemplary embodiments set forth herein are not to be construed as limiting the scope of the invention in any manner.

DETAILED DESCRIPTION OF THE INVENTION

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail in order to avoid unnecessary obscuring of the present invention.

Thus, all of the implementations described below are exemplary implementations provided to enable persons skilled in the art to make or use the embodiments of the disclosure and are not intended to limit the scope of the disclosure, which is defined by the claims. As used herein, the word "exemplary" or "illustrative" means "serving as an example, instance, or illustration." Any implementation described herein as "exemplary" or "illustrative" is not necessarily to be construed as preferred or advantageous over other implementations. Moreover, in the present description, the terms "upper", "lower", "left", "rear", "right", "front", "vertical", "horizontal", and derivatives thereof shall relate to the invention as oriented in FIG. 1.

Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
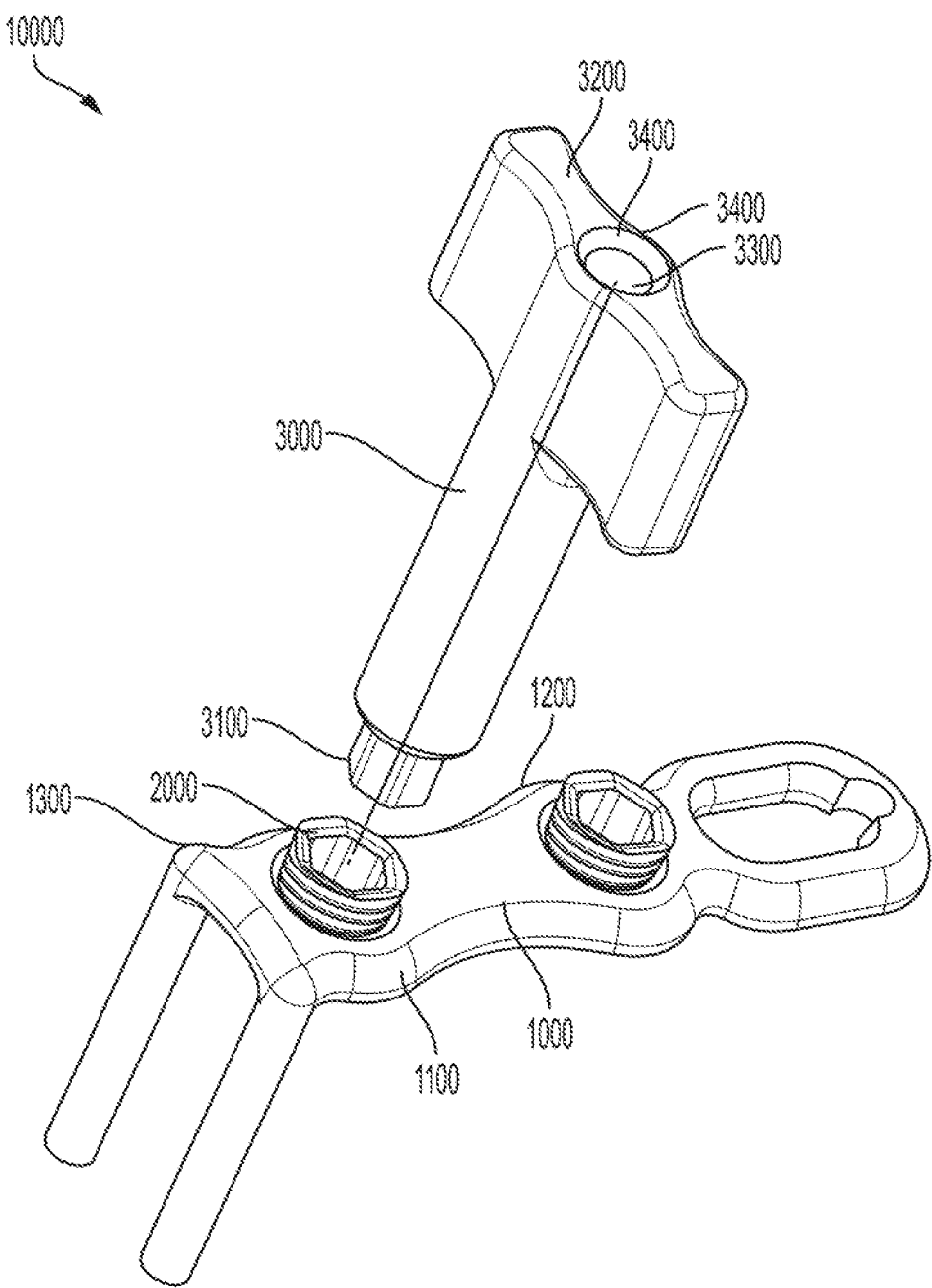
FIG. 1 shows a perspective view of a bone plate system in accordance with the present invention.
Figure 2:
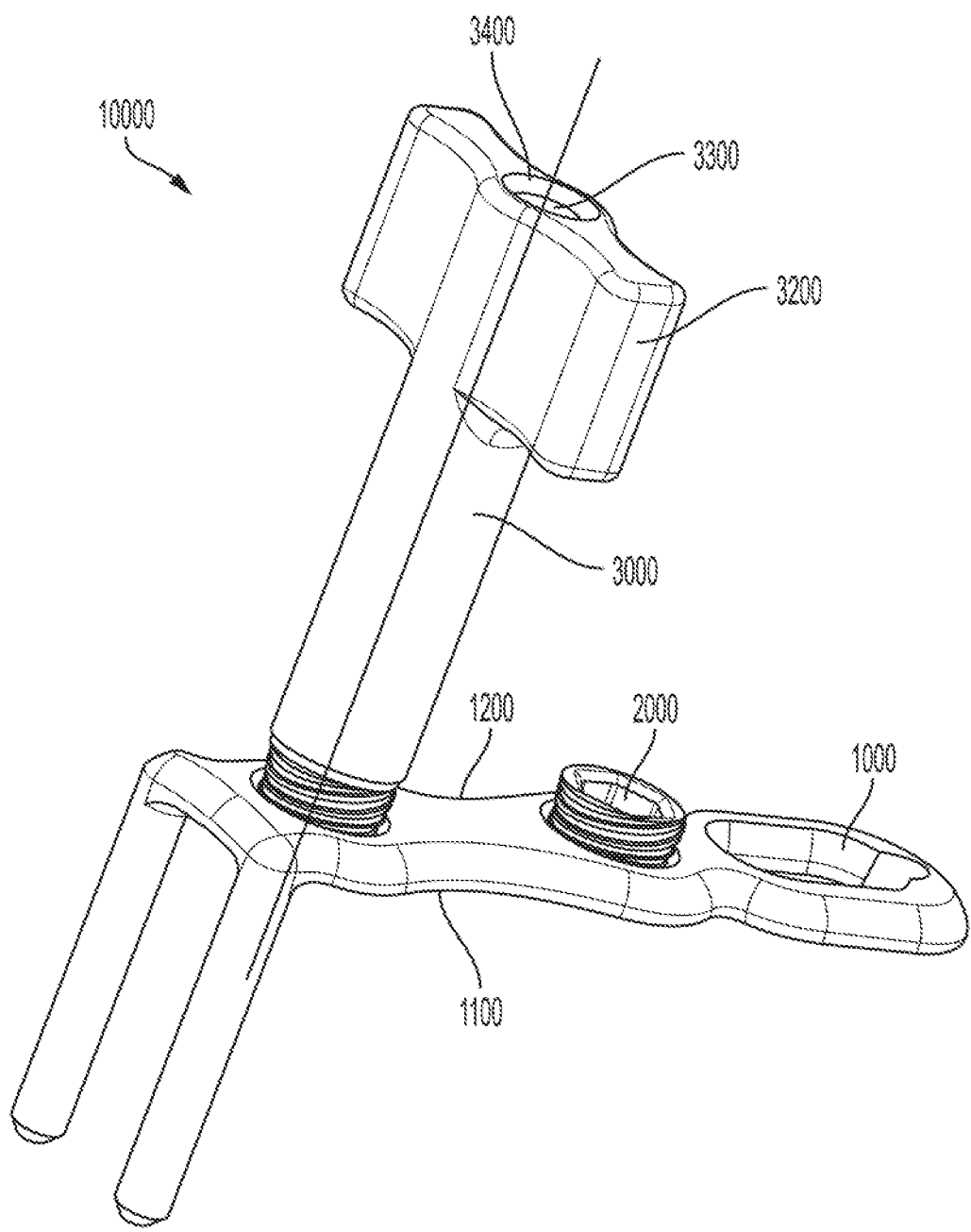
FIG. 2 shows a perspective view of the bone plate system of FIG. 1 with a guide tool engaged with a guide cap inserted in a bone plate.
Figure 3:
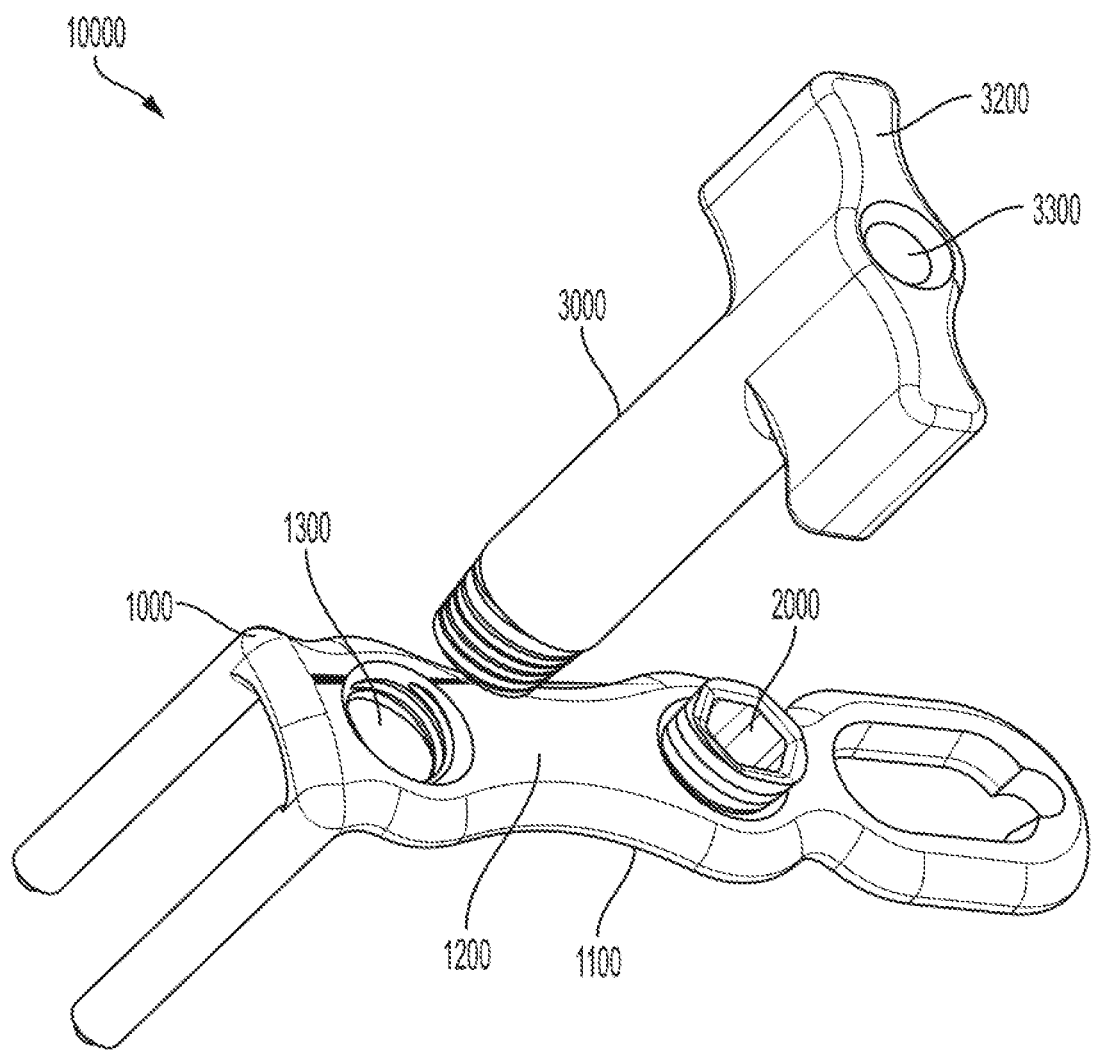
FIG. 3 shows a perspective view of the bone plate system of FIG. 1 with a guide tool engaged with the guide cap that has been removed from a bone plate.

Referring now generally to FIGS. 1-3, there is shown bone plate system 10000. Plate system 10000 generally includes a bone plate 1000, a plurality of guide caps 2000, and an insertion and extraction tool 3000. Insertion and extraction tool 3000 may be referred to as an insertion tool or an extraction tool but tool 3000 may perform both insertion and extraction functions. Insertion and extraction tool 3000 further has a tool longitudinal axis 3400 and an extraction tool bore 3300 extending axially. Bone plate 1000 is adapted for placement over the shaft of a bone (not shown). The term guide cap 2000 may also be referred to by terms "guide tip" or "guide pin" or guide plug.

Referring still to FIGS. 1-3, bone plate 1000 includes a generally flat shape, a bone contacting surface 1100 and a top surface 1200. Bone plate 1000 further includes a plurality of threaded holes 1300 for threadably receiving drill guide caps 2000. The holes are shown as cylindrical, but may be of any shape.

Referring now to FIGS. 1-3 and 5, each drill guide cap 2000 is shown with a generally cylindrical exterior shape. The drill guide cap need not be cylindrical and may be a tubular structure of any suitable perimeter shape. Each drill guide cap 2000 further includes an internal surface and an internal bore 2100 having a longitudinal axis 2200, a proximal end 2300, and a distal end 2400. Each drill guide cap 2000 preferably further includes a removal tool receiving opening at proximal end 2300. The removal tool receiving opening may be, for example, circular. Guide caps 2000 are used as a sole guide for a drill bit (not shown) for use with seating bone plate 1000 on a bone.

Referring again to FIGS. 1-3, insertion and extraction tool 3000 for drill guide caps 2000, includes a distal working end 3100 and a proximal drive handle end 3200. Guide caps 2000 may be inserted or extracted by insertion and extraction tool 3000. Distal working end 3100 preferably has a tapered square for engaging a circular opening at the proximal end 2300 of each drill guide cap 2000. The edges of the square driver are sized to provide sufficient frictional force to rotate the cap 2000 into and out of engagement with plate 1000. Other suitable engagements may be used as well. For example, guide caps 2000 may have a proximal end 2300 with a hex shape, or any non-circular exterior cross-sectional shape, that will facilitate torque transmission. When drill guide caps 2000 are connected to plate 1000 at a threaded hole 1300, using insertion and extraction tool 3000, the longitudinal axis 2200 of each guide cap 2000 may be coaxial with the axis of the respective threaded hole 1300 of plate 1000 in which the cap 2000 is inserted. Furthermore, extraction tool 3000 may be inserted into guide cap 2000 to a depth that may be at least the height of the guide cap cylinder 2000. When drill guide caps 2000 are connected to insertion and extraction tool 3000, the longitudinal axis 2200 and the tool longitudinal axis 3400 may be coaxial, such that extraction tool 3000 is generally perpendicular to bone plate 1000 when extracting or inserting drill guide caps 2000. The extraction tool 3000 may also be used as a drill guide when connected to guide caps 2000, and extraction tool 3000 may generally remain perpendicular to bone plate 1000 and coaxial to grill guide cap 2000 when used as a drill guide. Extraction tool 3000 may be used to facilitate placing a drill bit connected to a drill (not shown) into extraction tool bore 3300 and through drill guide cap 2000, for drilling into bone, when bone plate 1000 is positioned against the bone.

Referring still to FIGS. 1-3, in a preferred method of assembly, guide caps 2000 are threadably pre-assembled on plate 1000 in holes 1300. The pre-assembled plate 1000 and guide caps 2000 and are preferably supplied in a sterile package. Pre-assembly of the guide caps 2000 into the holes 1300 of plate 1000 is performed so that a surgeon does not have to thread the drill guide caps 2000 into plate 1000 before the plate 1000 is positioned on the bone during a surgical procedure. The pre-assembly can be done by the operating room technician or at the factory prior to packaging and sterilization.

Referring still to FIGS. 1-3, guide caps 2000 preferably include a hard, e.g., metal bore 2100. Guide caps 2000 may be made entirely of metal or have an outer plastic body with an insert such as a thin walled, molded metal tube. Additionally, guide caps 2000 may also be made entirely of plastic. Insertion/extraction tool 3000 may be made from hard metal. The insertion/extraction tool 3000 may be connectable to guide cap 2000, such that extraction tool 3000 may line the inner circumference or perimeter of guide cap 2000 for the height of guide cap 2000. Thus, when extraction tool 3000 is received in one of guide caps 2000 and the drill bit is introduced into extraction tool bore 3300 of extraction tool 3000, any material from guide cap 2000 in contact with the drill bit is minimized or eliminated during drilling. This minimal contact allows guide cap 2000 to be made of plastic due to minimal risk of plastic debris being produced during drilling. The ability to manufacture the guide caps 2000 from plastic reduces manufacturing cost, and the use of the insertion/extraction tool 3000 mitigates any risk of plastic debris generation due to contact between guide caps 2000 made from plastic and the drill bit.

Referring again to FIG. 3, after the drill bit has prepared a hole, the extraction tool may be turned to unscrew cap 2000. Cap 2000 and extraction tool 3000 are adapted to be separable when a first axial force is applied to cap 2000 along longitudinal axis 2200 in a first direction and a second force is applied to tool 3000 along the longitudinal axis 2200 in a second direction, where the second direction is opposite the first direction. Thus, guide caps 2000 preferably are retained on extraction tool 3000 until pulled apart, after which, the extraction tool 3000 may be used for the next hole.

Figure 4:
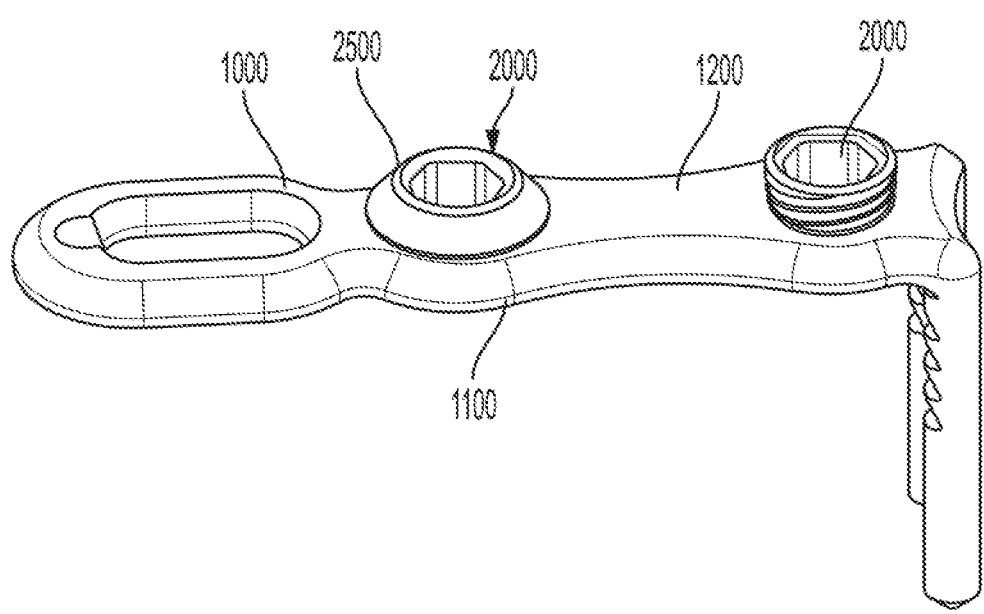
FIG. 4 shows a close-up perspective view of FIG. 1 including the bone plate with inserted guide caps.
Figure 5:
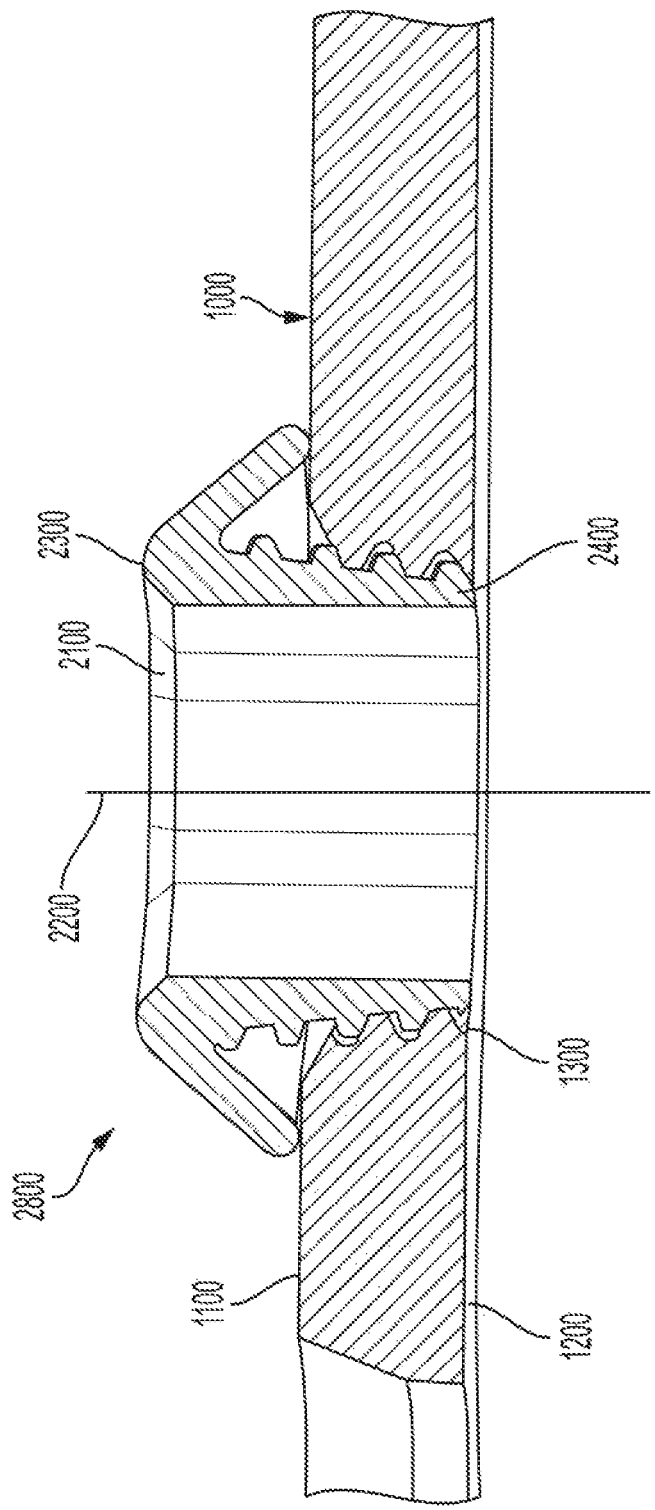
FIG. 5 shows a cross-sectional view of FIG. 1 including the bone plate with inserted guide caps.

Referring now to FIGS. 4-5, guide cap 2000 further has a flexible flange 2800 extending from and around proximal end 2300 of guide cap 2000. Flange 2800 extends from proximal end 2300 of guide cap 2000 toward distal end 2400 and forms an acute angle between the threaded exterior portion of guide cap 2000 and flange 2800.

The flange 2800 or "umbrella top" feature may be on the proximal portion 2300 of guide cap 2000. A combination of this umbrella top feature, the plate 1000, and cap 2000 has nearly no lip edge and thus may be easier for user to slide the assembled construct of guide cap 2000 and bone plate 1000 under soft tissue. The umbrella top is also flexible which allows it to flex and adapt to thicker or thinner plates 1000; thus, the same guide pin 2000 can be used for a variety of plate (e.g. plate 1000) thicknesses instead of having to fit a uniquely sized guide cap 2000 to each individual plate (e.g. plate 1000) thickness.

One advantage of the present invention, is the low profile of guide caps 2000 connected to plate 1000, compared to the prior art. The term "low profile" is understood to mean minimally extending from the bone surface. This makes the placement of plate 1000 much easier, compared to the prior art, because in some surgical procedures require a surgeon to slide a plate under an incision or under a tendon/ligament. Other pre-assembled plate and guide combinations are too tall thus requiring the surgeon to remove the assembled guides from the assembly and replace the guides once the plate is positioned on the anatomy, thereby defeating the purpose of a pre-assembled plate. The present system 10000 maintains a low profile until pre-assembled plate 1000 and guide caps 2000 are in place under whatever anatomy is required. In one embodiment, the guide caps may be equal to or less that the thickness of the bone plate. In other embodiments, the presence of a flexible flange 2800, may make the guide cap 2000 extend above the bone plate surface by approximately 1.5 mm or less. Thus, the guide caps 2000 either do not add to the thickness of the plate or in other embodiments, only minimally add to the thickness.

Another advantage is that extraction tool 3000 for guide caps 2000 is built into the drill guide cap 2000 and removal tool 3000 combination. This may help to minimize wait and preparation times between the surgical steps. For example, in the prior art, drill guide caps or pins are removed using a surgical screw driver, commonly the one used to insert surgical screws. In an embodiment of this invention, the extraction tool 3000 may be an extension of the guide caps 2000, for drilling and guide cap removal. While the extraction tool 3000 may be used to remove guide caps 2000, the surgical screw driver may be prepared for inserting screws, thus minimizing wait and preparation times. Other systems in the prior art require guide caps to be removed with the surgical screw driver that is also used to insert the screw which means the two processes must be done in series thus requiring more time.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. A bone plate system for use with fasteners for fixation of a fractured bone, said system comprising:
   a bone plate for placement on the bone, said bone plate comprising:
      an elongate shaft for placement against a bone, at least one threaded hole for receiving a fastener, each of said at least one threaded hole comprising a central axis,
      a bone contacting first surface,
      an opposite second surface, and a thickness extending in a direction between said first and second surfaces; and
   at least one tubular drill guide cap, engageable with a first hole of said at least one threaded hole, said cap comprising a threaded exterior, an internal bore, a proximal end, and a distal end opposite said proximal end and engageable with said first hole; and
   said at least one tubular drill guide cap comprising a flexible flange around said proximal end, said flange extending from said proximal end toward said distal end and toward said plate when said distal end engages said first hole, said flange extending along flange longitudinal axis from said proximal end toward said second surface when said distal end engages said first hole, said flange longitudinal axis forming an acute angle with a longitudinal axis of the tubular drill guide cap and wherein the flexible flange contacts said second surface of the bone plate when said tubular drill guide cap is installed in said at least one threaded hole of the bone plate.

2. The bone plate system of claim 1, wherein said flange comprises a flange proximal end connected to said proximal end and a flange distal end opposite said flange proximal end, said flange distal end radially spaced from said threaded exterior.

3. A bone plate system for use with fasteners for fixation of a fractured bone, said system comprising:

a bone plate for placement on the bone, said bone plate comprising an elongate shaft for placement against a bone, said bone plate further comprising at least one threaded hole for receiving a fastener, each of said at least one threaded holes comprising a central axis, said plate further comprising a bone contacting first surface, an opposite second surface, and a thickness extending in a direction between said first and second surfaces;

at least one tubular drill guide cap, engageable with a first hole of said at least one threaded hole, said cap comprising a threaded exterior, an internal bore, a proximal end, a distal end opposite said distal end, and a flange extending from said proximal end toward said second surface of said plate when said cap engages said first hole;

a cap removal tool, said cap removal tool comprising a proximal end, a tool longitudinal axis and a distal end, the tool longitudinal axis and the central axis being coaxial, said distal end shaped to engage said proximal end of said cap, said cap and said cap removal tool being releasably connectable; and said cap removal tool having a tool bore therethrough configured to guide a drill bit through said cap removal tool and into the bone.

4. The bone plate system of claim 3, wherein flange comprises a flexible flange around said proximal end, said flange forming an acute angle between said threaded exterior portion of said cap and said flange.

5. The bone plate system of claim 3, wherein said cap and said tool are separable when a first axial force is applied to said cap along said central axis in a first direction and a second force is applied to said tool along said central axis in a second direction, where said second direction is opposite said first direction.

6. A method for fixation of a fractured bone, the method steps comprising:
   providing alignment drill guide caps preassembled on a bone plate;
   providing an extraction tool, the extraction tool having a tool longitudinal axis and an extraction tool bore, with the extraction tool bore extending along a length of the tool;
   inserting the extraction tool into a cap bore of a first drill guide cap of the drill guide caps, said first drill guide cap received in a threaded hole of the bone plate;
   using the extraction tool to guide a drill by extending a drill bit through the extraction tool bore;
   drilling a hole in the bone using the drill;
   removing the drill bit from the bore;
   rotating the extraction tool to remove the drill guide cap from the bone plate, and
   inserting a fastener through the hole to fix the bone plate to the bone.

7. The method of claim 6 wherein the drill guide cap comprises a threaded exterior, an internal bore, a proximal end, and a distal end opposite the proximal end and received in the threaded hole; and
   the drill guide cap comprising a flexible flange around the proximal end, the flange extending from the proximal end toward the distal end and toward the plate, the flexible flange extending along a flange longitudinal axis from the proximal end of the drill guide cap towards the second surface of the plate when the distal end engages the first hole, the longitudinal axis forming an acute angle with a longitudinal axis of the drill guide cap.

* * * * *